(12) United States Patent
Matsukawa

(10) Patent No.: US 9,575,002 B2
(45) Date of Patent: Feb. 21, 2017

(54) LIGHT STIMULATION DEVICE AND MICROSCOPE SYSTEM

(71) Applicant: OLYMPUS CORPORATION, Shibuya-ku, Tokyo (JP)

(72) Inventor: Yasunari Matsukawa, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 183 days.

(21) Appl. No.: 14/549,283

(22) Filed: Nov. 20, 2014

(65) Prior Publication Data

US 2015/0192766 A1 Jul. 9, 2015

(30) Foreign Application Priority Data

Jan. 7, 2014 (JP) .................................. 2014-000935

(51) Int. Cl.
*H01J 5/16* (2006.01)
*G01N 21/64* (2006.01)
*G02B 21/00* (2006.01)

(52) U.S. Cl.
CPC ....... *G01N 21/6428* (2013.01); *G02B 21/0032* (2013.01); *G02B 21/0076* (2013.01); *G02B 2207/114* (2013.01)

(58) Field of Classification Search
CPC .............................................. G02B 21/0032
USPC ................................ 250/216, 201.1; 359/385
See application file for complete search history.

(56) References Cited

U.S. PATENT DOCUMENTS

2013/0250391 A1\* 9/2013 Kato .................... G02B 21/082
359/238

FOREIGN PATENT DOCUMENTS

JP 2011133580 A 7/2011

\* cited by examiner

*Primary Examiner* — Thanh Luu
(74) *Attorney, Agent, or Firm* — Holtz, Holtz & Volek PC

(57) ABSTRACT

The number of stimulated spots and/or the area of a stimulated spot is easily increased or decreased while keeping the irradiation power for each stimulated spot constant. Provided is a light stimulation device (3) that includes an objective lens (23) that radiates stimulation light emitted from a stimulation laser (11) onto a specimen (S); an LCOS-SLM (17) that is located at a position conjugate to the pupil of the objective lens (23) and that can modulate the phase of stimulation light to be made to enter the objective lens (23) based on a predetermined pupil modulation pattern; an AOM (13) that adjusts the amount of stimulation light to be made to enter the LCOS-SLM (17); a mouse (26) that is used to specify the number of spots and the position of a spot of light to be radiated onto the specimen (S); and a controller main unit (28) that determines the pupil modulation pattern for the LCOS-SLM (17) according to the number of spots and the position of a spot specified by means of the mouse (26) and that controls the AOM (13) such that, when the number of spots specified by means of the mouse (26) is changed, the amount of light to be radiated onto each spot before and after the change in the number of spots becomes constant.

4 Claims, 3 Drawing Sheets

LIGHT STIMULATION DEVICE AND MICROSCOPE SYSTEM

CROSS-REFERENCE TO RELATED APPLICATIONS

This application is based on Japanese Patent Application No. 2014-000935, the contents of which are incorporated herein by reference.

TECHNICAL FIELD

The present invention relates to a light stimulation device and a microscope system.

BACKGROUND ART

Conventionally, pupil modulation techniques using an LCOS-SLM (Liquid Crystal On Silicon-Spatial Light Modulator) have been known (for example, see PTL 1). A phase-modulation-type spatial light modulating device using an LCOS device can desirably change the phase distribution of light to be made to enter the pupil of an objective lens and can simultaneously form multiple spots at an image position. With an LCOS device, the sum of the energy of diffracted light transmitted through the pupil of the objective lens and the energy of light focused at the image position is constant in theory, and the power of the light can be efficiently used.

CITATION LIST

Patent Literature

{PTL 1} Japanese Unexamined Patent Application, Publication No. 2011-133580

SUMMARY OF INVENTION

Technical Problem

When a specimen is stimulated with light by the LCOS device, because the number of spots and irradiation power are correlated, the power of stimulation light for each stimulated spot is decreased in inverse proportion to the number of stimulated spots. Therefore, in order to increase the number of stimulated spots with the same irradiation power or in order to decrease the number of stimulated spots while keeping the same irradiation power, the setting for the stimulated spots and the irradiation power need to be changed in association with each other, which requires an extremely troublesome operation.

The present invention provides a light stimulation device and a microscope system capable of easily increasing or decreasing the number of stimulated spots or the area of a stimulated spot while keeping the irradiation power for each stimulated spot constant.

Solution to Problem

According to a first aspect, the present invention provides a light stimulation device including: an objective lens that radiates light emitted from a light source onto a specimen; a phase modulating section that is located at a position conjugate to a pupil of the objective lens and that can modulate the phase of light to be made to enter the objective lens, based on a predetermined pupil modulation pattern; a light-amount adjusting section that adjusts the amount of light to be made to enter the phase modulating section; a spot specifying section that is used to specify the number of spots and/or a spot area and a spot position of light to be radiated onto the specimen by the objective lens; a pupil-modulation-pattern determining section that determines the pupil modulation pattern for the phase modulating section according to the number of spots and/or the spot area and the spot position specified by means of the spot specifying section; and a light-amount control section that controls the light-amount adjusting section such that, when the number of spots and/or the spot area specified by means of the spot specifying section is changed, the amount of light to be radiated onto each spot before and after the change in the number of spots and/or the spot area becomes constant.

According to this aspect, the pupil-modulation-pattern determining section determines the pupil modulation pattern according to the number of spots and/or the spot area and the spot position specified by means of the spot specifying section. Furthermore, light whose amount has been adjusted by the light-amount adjusting section is phase-modulated by the phase modulating section based on the pupil modulation pattern and is radiated onto the specimen by the objective lens. Thus, it is possible to simultaneously apply light stimulation to a plurality of radiation positions in the specimen, corresponding to the pupil modulation pattern of the phase modulating section.

In this case, when the number of spots and/or the spot area specified by means of the spot specifying section is changed, the light-amount control section controls the light-amount adjusting section to radiate a constant amount of light onto each spot before and after the change in the number of spots and/or the spot area. Thus, regardless of an increase or decrease in the number of spots and/or the spot area, it is possible to keep applying light stimulation to each spot at a desired constant intensity. Therefore, the number of stimulated spots and the area of a stimulated spot can be easily increased or decreased while keeping the irradiation power for each stimulated spot constant.

In the above-described aspect, the light-amount control section may control the light-amount adjusting section so as to increase or decrease the amount of light to be made to enter the phase modulating section in direct proportion to an increase or decrease in the number of spots and/or the spot area.

With this configuration, if the irradiation power to be distributed to each spot is increased or decreased in inverse proportion to an increase or decrease in the number of spots and/or the spot area, the irradiation power for each spot can be easily corrected.

In the above-described aspect, the light-amount control section may have a table in which the number of spots and/or the spot area is associated with a value indicating the amount of light to be made to enter the phase modulating section and may control the light-amount adjusting section according to the table.

With this configuration, even if an increase or decrease in the number of spots and/or the spot area and an increase or decrease in the irradiation power to be distributed to each spot do not have an inversely proportional relationship, the irradiation power for each spot can be easily and accurately corrected.

According to a second aspect, the present invention provides a microscope system including: an imaging device that includes: a scanning section that scans excitation light emitted from a light source on a specimen; and an image forming section that detects return light returning from the specimen when the excitation light is scanned by the scanning section and that forms an image of the specimen; and one of the above-described light stimulation devices.

According to this aspect, the reaction of the specimen that has been subjected to simultaneous stimulation by the light stimulation device with the irradiation power for each spot kept constant while the number of spots and/or the spot area is increased or decreased can be observed on an image by the imaging device.

Advantageous Effects of Invention

According to the present invention, an advantageous effect is afforded in that it is possible to easily increase or decrease the number of stimulated spots or the area of a stimulated spot while keeping the irradiation power for each stimulated spot constant.

DESCRIPTION OF EMBODIMENTS

First Embodiment

A light stimulation device and a microscope system according to a first embodiment of the present invention will be described below with reference to the drawings.

Figure 1:
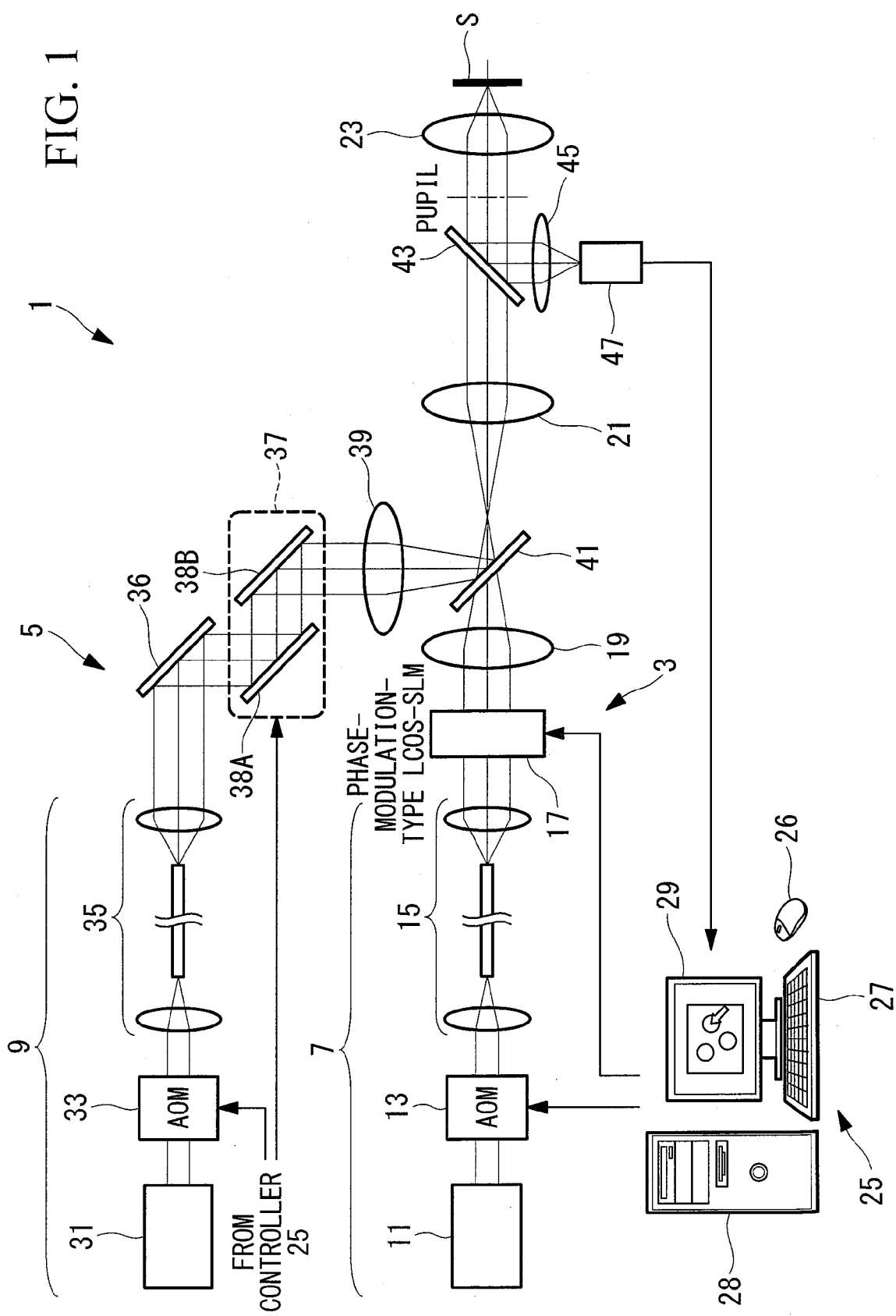
FIG. 1 is a view showing, in outline, the configuration of a microscope system according to a first embodiment of the present invention.

As shown in FIG. 1, a multiphoton excitation (MPE) laser microscope system (hereinafter, referred to as microscope system) 1 according to this embodiment includes a light stimulation device 3 that applies light stimulation to a specimen S and an imaging device 5 that generates an image of the specimen S.

The light stimulation device 3 includes an illumination means 7 for emitting stimulation laser light (hereinafter, referred to as stimulation light) to be radiated onto the specimen S, an LCOS-SLM (Liquid Crystal On Silicon-Spatial Light Modulator, phase modulating section) 17 that can modulate the phase of the stimulation light emitted from the illumination means 7, and a pupil projection lens 19 that focuses the stimulation light transmitted through the LCOS-SLM 17.

The illumination means 7 includes an ultrashort pulsed laser (light source; hereinafter, referred to as stimulation laser) 11 that emits stimulation light, an AOM (Acousto-Optic Modulator, acousto-optic element, light-amount adjusting section) 13 that performs on/off control and intensity control of the stimulation light emitted from the stimulation laser 11, and a guiding optical system 15 that converts the stimulation light transmitted through the AOM 13 into collimated light.

Furthermore, the light stimulation device 3 includes an imaging lens 21 that converts the stimulation light focused by the pupil projection lens 19 into collimated light, an objective lens 23 that radiates the stimulation light converted into collimated light by the imaging lens 21 onto the specimen S and that collects light returning from the specimen S, and a controller 25 that performs control of the AOM 13, the LCOS-SLM 17, and other types of control. The light stimulation device 3 can apply light stimulation to the specimen S at desired timing regardless of whether the imaging device 5 is being operated or not.

The imaging device 5 includes an illumination means 9 for emitting excitation laser light (hereinafter, referred to as excitation light) to be radiated onto the specimen S, a reflective mirror 36 that reflects the excitation light emitted from the illumination means 9, a scanner (scanning section) 37 that deflects the excitation light reflected by the reflective mirror 36, a pupil projection lens 39 that focuses the excitation light deflected by the scanner 37, and a combining DM (Dichroic Mirror) 41 that combines the excitation light focused by the pupil projection lens 39 in the light path of the stimulation light of the light stimulation device 3.

The illumination means 9 includes an ultrashort pulsed laser (light source; hereinafter, referred to as excitation laser) 31 that emits excitation light, an AOM 33 that performs on/off control and intensity modulation of the excitation light emitted from the excitation laser 31, and a guiding optical system 35 that converts the excitation light transmitted through the AOM 33 into collimated light.

Furthermore, the imaging device 5 also uses the imaging lens 21, the objective lens 23, and the controller 25 of the light stimulation device 3, and thus the excitation light combined in the light path of the stimulation light by the combining DM 41 is converted into collimated light by the imaging lens 21 and is radiated onto the specimen S by the objective lens 23. Furthermore, in the imaging device 5, the controller 25 controls the AOM 33 and the scanner 37 and generates an image of the specimen S.

Furthermore, the imaging device 5 includes an excitation DM 43 that separates, from the light path of the light stimulation device 3, fluorescence that is produced in the specimen S by radiating the excitation light onto the specimen S and that is collected by the objective lens 23; a focusing lens 45 that focuses the fluorescence separated by the excitation DM 43; and a PMT (Photomultiplier Tube) 47 that detects the fluorescence focused by the focusing lens 45, performs photoelectric conversion thereon, and sends a light-intensity signal corresponding to the brightness to the controller 25.

Under the control of the controller 25, the AOMs 13 and 33 can perform on/off switching of irradiation of stimulation light emitted from the stimulation laser 11 and excitation light emitted from the excitation laser 31 onto the specimen S and can adjust the amount of stimulation light to be made to enter the LCOS-SLM 17 and the amount of excitation light to be made to enter the scanner 37.

The LCOS-SLM 17 has 1920×1080 pixels (not shown), for example, and is located at a position conjugate to the pupil position of the objective lens 23. Furthermore, under the control of the controller 25, the LCOS-SLM 17 can desirably change, at each of the pixels, the phase of stimulation light within the range from 0 to $2\pi$ [rad] and can allow the stimulation light to be transmitted therethrough. Thus, the LCOS-SLM 17 can three-dimensionally change the intensity distribution of the stimulation light on the specimen S and can radiate a desired three-dimensional pattern, serving as a Fourier transform image, onto the specimen S.

The scanner 37 is a so-called proximity galvanometer scanner and includes two galvanometer mirrors 38A and 38B disposed facing each other. Under the control of the controller 25, the scanner 37 makes the two galvanometer mirrors 38A and 38B swivel about axes (XY) perpendicular to each other to cause raster-scan movement, thereby deflecting the excitation light. Thus, the scanner 37 can two-dimensionally scan the excitation light on the specimen S.

The combining DM 41 transmits the stimulation light focused by the pupil projection lens 19 of the light stimulation device 3 and reflects the excitation light focused by the pupil projection lens 39 of the imaging device 5, thereby combining the light path of the stimulation light with the light path of the excitation light.

The excitation DM 43 transmits the stimulation light or the excitation light coming from the imaging lens 21 to make it enter the objective lens 23 and also reflects fluorescence coming from the specimen S and collected by the objective lens 23 toward the focusing lens 45, thereby separating the light path of the fluorescence from the light path of the excitation light.

The controller 25 includes a mouse 26 and a keyboard 27 (each of which is a spot specifying section) with which a user inputs an instruction; a controller main unit (pupil-modulation-pattern determining section, light-amount control section) 28 that controls the AOM 13, the AOM 33, the LCOS-SLM 17, and the scanner 37 and that generates an image; and a monitor 29 that displays the image etc.

Through manipulation of the mouse 26 and the keyboard 27 by the user, the number of spots, the spot positions, etc. of stimulation light to be radiated onto the specimen S can be specified.

The controller main unit 28 determines the pupil modulation pattern for the LCOS-SLM 17 according to the number of spots and the spot positions specified by means of the mouse 26 or the keyboard 27.

Furthermore, when the number of spots is changed while keeping the spot area of stimulation light constant, the controller main unit 28 controls the AOM 13 to increase or decrease the amount of stimulation light to be made to enter the LCOS-SLM 17 in direct proportion to an increase or decrease in the number of spots.

For example, when the number of spots of stimulation light is increased, the controller main unit 28 increases the amount of stimulation light to be made to enter the LCOS-SLM 17 in direct proportion to the increase in the number of spots. Furthermore, when the number of spots of stimulation light is decreased, the controller main unit 28 decreases the amount of stimulation light to be made to enter the LCOS-SLM 17 in direct proportion to the decrease in the number of spots.

When the required amount of stimulation light reaches an upper limit of the stimulation laser 11 after an increase in the number of spots, the controller main unit 28 may clip a signal for increasing the amount of stimulation light or may inform the user that the amount by which the stimulation light can be increased has reached its limit, by displaying this fact on the monitor 29.

Furthermore, the controller main unit 28 accumulates light-intensity signals sent from the PMT 47, at respective pixels corresponding to scanning positions of the scanner 37, to generate a two-dimensional image of the specimen S. The controller main unit 28 can cause the monitor 29 to display the generated image.

The effects of the thus-configured light stimulation device 3 and microscope system 1 will now be described.

In order to acquire an image of the specimen S by the imaging device 5 of the microscope system 1 according to this embodiment, excitation light is emitted from the excitation laser 31, and the AOM 33 switches on irradiation of the excitation light onto the specimen S and modulates the excitation light. The excitation light modulated by the AOM 33 is deflected by the scanner 37 via the guiding optical system 35 and the reflective mirror 36, is focused by the pupil projection lens 39, and is combined in the light path of the light stimulation device 3 by the combining DM 41.

The excitation light combined in the light path of the light stimulation device 3 is converted into collimated light by the imaging lens 21, is transmitted through the excitation DM 43, and is radiated onto the specimen S by the objective lens 23. Thus, the excitation light is two-dimensionally scanned on the specimen S according to the swivel angles of the galvanometer mirrors 38A and 38B of the scanner 37.

When fluorescence is produced in the specimen S through irradiation of the excitation light, the fluorescence is collected by the objective lens 23. The fluorescence collected by the objective lens 23 is separated from the light path of the excitation light by the excitation DM 43 and is detected by the PMT 47 via the focusing lens 45. In the PMT 47, the detected fluorescence is subjected to photoelectric conversion, and a light-intensity signal corresponding to the brightness is sent to the controller main unit 28 of the controller 25.

The controller main unit 28 accumulates light-intensity signals sent from the PMT 47, at respective pixels corresponding to scanning positions of the scanner 37, to generate a two-dimensional image of the specimen S and causes the monitor 29 to display the generated image. Thus, the user can observe the specimen S on the monitor 29.

Next, in order to apply light stimulation to the specimen S by the light stimulation device 3, the user first specifies the number of spots of stimulation light and the spot positions by means of the mouse 26 or the keyboard 27. Then, a pupil modulation pattern for the LCOS-SLM 17 is determined by the controller main unit 28 according to the specified number of spots and spot positions.

Then, stimulation light is emitted from the stimulation laser 11, and the AOM 13 switches on irradiation of the stimulation light onto the specimen S and modulates the stimulation light. The stimulation light modulated by the AOM 13 enters the LCOS-SLM 17 via the guiding optical system 15, is phase-modulated based on the pupil modulation pattern determined by the controller main unit 28, and is transmitted through the LCOS-SLM 17.

The stimulation light transmitted through the LCOS-SLM 17 is focused by the pupil projection lens 19, is transmitted through the combining DM 41, and is converted into collimated light by the imaging lens 21. The stimulation light converted into collimated light is transmitted through the excitation DM 43 and is radiated onto the specimen S by the objective lens 23. Thus, light stimulation can be simultaneously applied to a plurality of irradiated positions on the specimen S based on the intensity distribution of a pattern corresponding to the amount of phase modulation in the LCOS-SLM 17.

For example, the light stimulation device 3 applies light stimulation to the specimen S while the imaging device 5 acquires an image of the specimen S, thereby making it possible to observe the reaction of the specimen S to light stimulation, on the monitor 29.

Furthermore, when the user changes the number of spots of stimulation light and the spot positions by means of the mouse 26 or the keyboard 27, the amount of phase modulation of the stimulation light in the LCOS-SLM 17 is changed by the controller main unit 28, and light stimulation can be simultaneously applied to a plurality of irradiated positions on the specimen S based on another pattern having a different intensity distribution.

Here, when light stimulation is applied to the specimen S by the LCOS-SLM 17, the sum of the energy of diffracted light transmitted through the pupil of the objective lens 23 and the energy of light focused at the image position is almost constant, and the number of spots and the irradiation power show a correlation.

In the light stimulation device 3 of this embodiment, when the number of spots is changed while keeping the spot area of stimulation light constant, the controller main unit 28 controls the AOM 13 to increase or decrease the amount of stimulation light to be made to enter the LCOS-SLM 17 in direct proportion to an increase or decrease in the number of spots.

For example, when the number of spots of stimulation light is increased from $N_1$ to $N_2$, the AOM 13 increases the amount of stimulation light by a factor $N_2/N_1$ in direct proportion to the increase in the number of spots. On the other hand, when the number of spots is decreased from $N_2$ to $N_1$, the AOM 13 decreases the amount of stimulation light by a factor $N_1/N_2$ in direct proportion to the decrease in the number of spots.

Thus, it is possible to avoid a situation in which irradiation power to be distributed to each spot is increased or decreased in inverse proportion to an increase or decrease in the number of spots and to radiate a constant amount of stimulation light onto each spot before and after the change in the number of spots. Therefore, regardless of an increase or decrease in the number of spots, it is possible to keep applying light stimulation to each spot at a desired constant intensity.

As described above, according to the light stimulation device 3 and the microscope system 1 of this embodiment, when the number of spots of stimulation light is changed, the controller main unit 28 controls the AOM 13 such that a constant amount of stimulation light is radiated onto each spot before and after the change in the number of spots, thereby making it possible to easily increase or decrease the number of stimulated spots while keeping the irradiation power for each stimulated spot constant. Furthermore, the reaction of the specimen S that has been subjected to light stimulation can be observed on the monitor 29 by the imaging device 5.

This embodiment can be modified as described below.

Specifically, in this embodiment, the controller main unit 28 controls the AOM 13 so as to increase or decrease the amount of stimulation light in direct proportion to an increase or decrease in the number of spots of stimulation light. As one modification, the controller main unit 28 may have a table K in which the number of spots and the amount of stimulation light for each spot are associated with each other, such as that shown in FIG. 2, and may control the AOM 13 according to the table K.

The table K may be obtained such that, for example, when the number of spots is changed to $N_1, N_2, N_3, \ldots,$ and $N_{max}$ while keeping the spot area constant, the amounts of stimulation light $Y_1, Y_2, Y_3, \ldots,$ and $Y_{min}$ for each spot are measured by a light power meter or the like, and the measured values are associated with the numbers of spots. $N_{max}$ is an upper limit of the number of multipoint ROIs that can be registered in the system.

For example, when the number of spots is changed from $N_1$ to $N_2$ while keeping the spot area constant, the controller main unit 28 can cause the AOM 13 to multiply the amount of stimulation light to be made to enter the LCOS-SLM 17 by $Y_1/Y_2$ based on the table K. Specifically, if the amount of stimulation light to be made to enter the LCOS-SLM 17 is $P_1$ when the number of spots is $N_1$, the amount of stimulation light $P_2$ to be made to enter the LCOS-SLM 17 when the number of spots is changed to $N_2$ can be obtained by multiplying $P_1$ by $(Y_1/Y_2)$.

Figure 2:
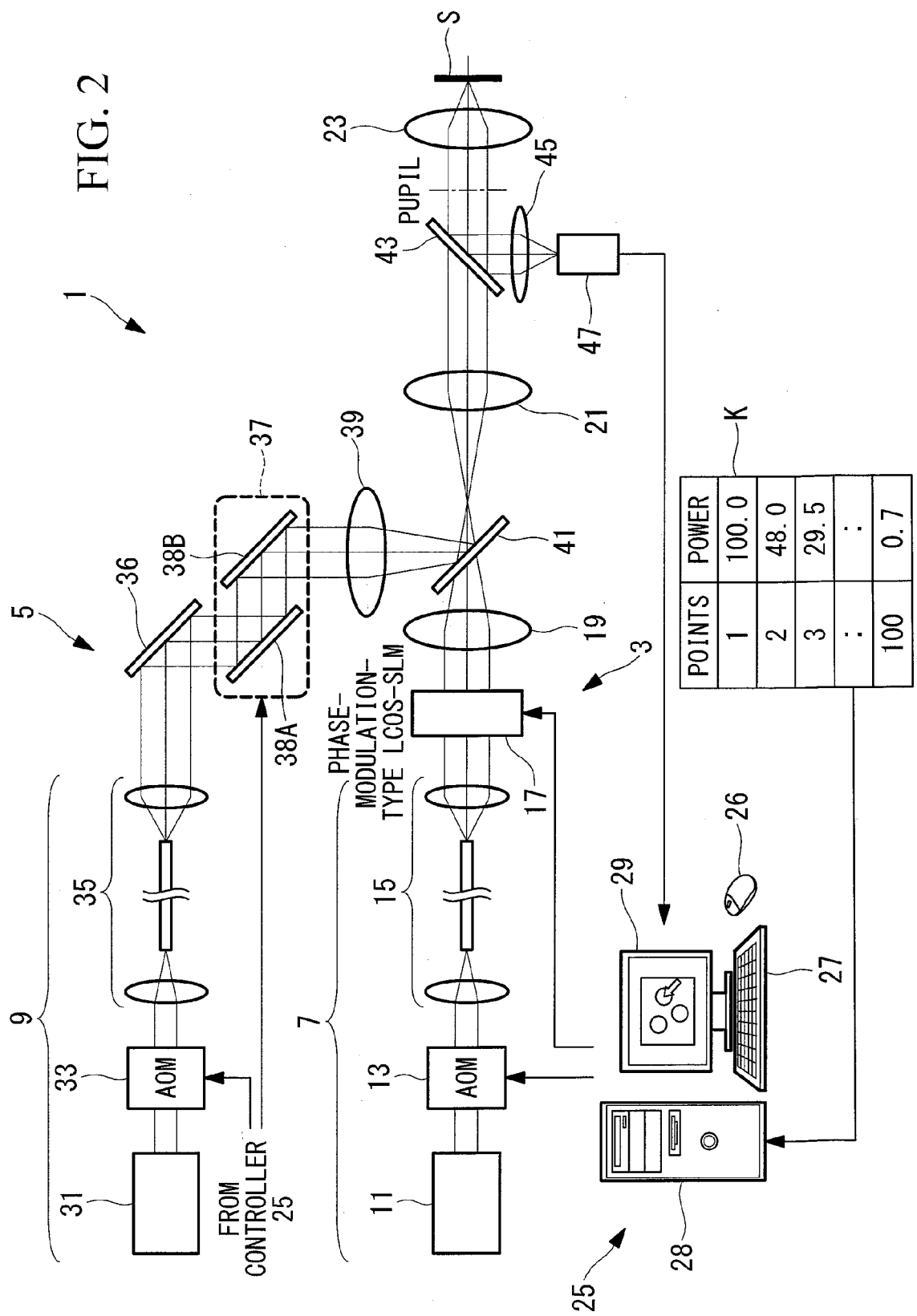
FIG. 2 is a view showing, in outline, the configuration of a microscope system according to one modification of the first embodiment of the present invention.

In an example shown in FIG. 2, for example, when the number of spots is changed from one to two, the amount of stimulation light for each spot is changed from 100.0 to 48.0. Therefore, the amount of stimulation light $P_2$ to be made to enter the LCOS-SLM 17 when the number of spots is two can be obtained by multiplying the amount of stimulation light $P_1$ to be made to enter the LCOS-SLM 17 when the number of spots is one by 100.0/48.0 (by about 2.08).

Furthermore, for example, when the number of spots is changed from two to three, the amount of stimulation light for each spot is changed from 48.0 to 29.5. Therefore, the amount of stimulation light $P_3$ to be made to enter the LCOS-SLM 17 when the number of spots is three can be obtained by multiplying the amount of stimulation light $P_2$ to be made to enter the LCOS-SLM 17 when the number of spots is two by 48.0/29.5 (by about 1.63).

By doing so, even if an increase or decrease in the number of spots of stimulation light and an increase or decrease in the irradiation power to be distributed to each spot do not have an inversely proportional relationship, it is possible to easily and accurately correct the irradiation power for each spot, including an error slightly deviating from the inversely proportional relationship.

In this modification, it is also possible to provide, instead of the table K, a table (not shown) in which the number of spots of stimulation light is associated with the amount of stimulation light to be made to enter the LCOS-SLM 17. By doing so, the controller main unit 28 can control the AOM 13 by using the amount of stimulation light included in the table as it is, thus facilitating the processing.

Second Embodiment

Next, a light stimulation device and a microscope system according to a second embodiment of the present invention will be described.

Figure 3:
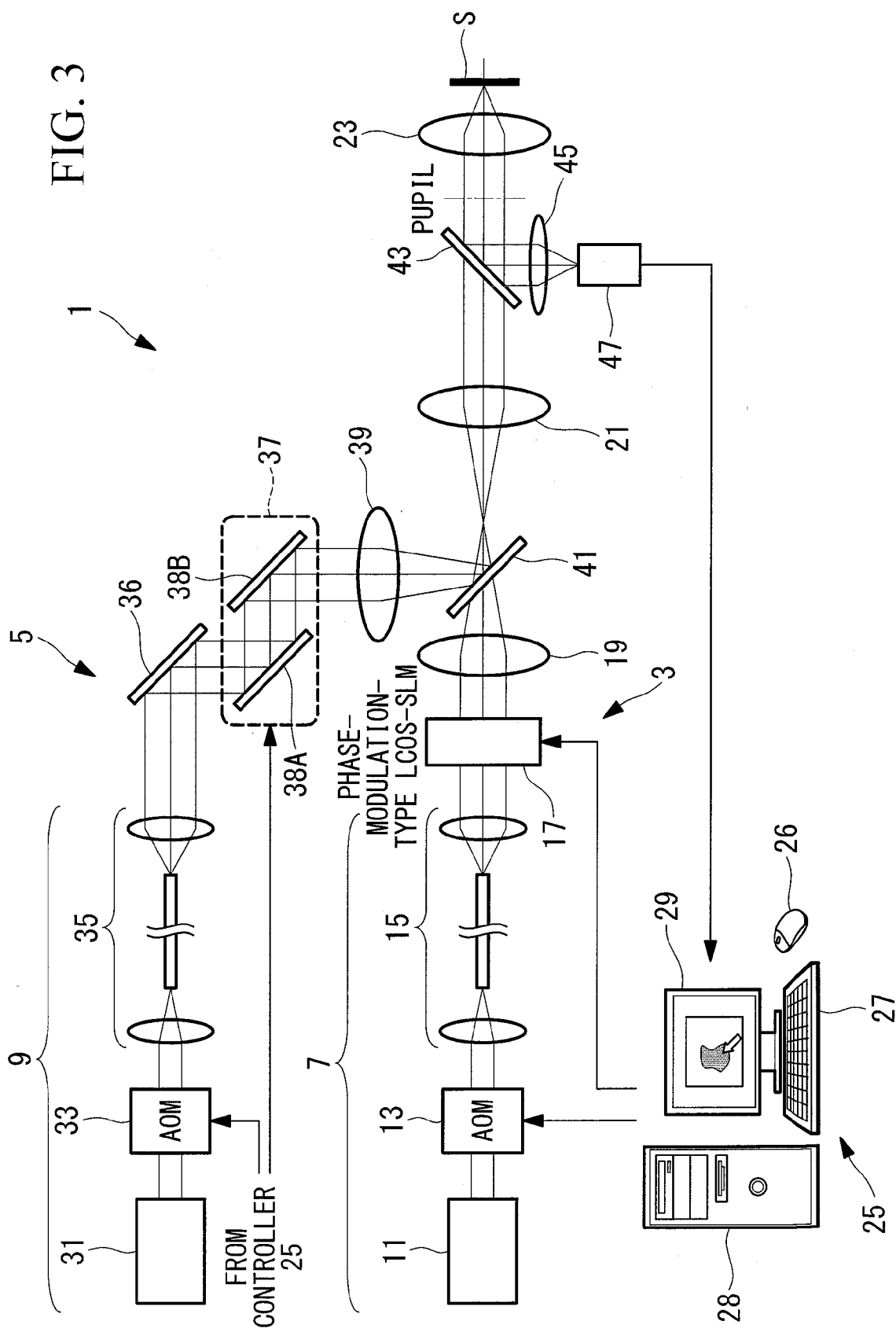
FIG. 3 is a view showing, in outline, the configuration of a microscope system according to a second embodiment of the present invention.

As shown in FIG. 3, the microscope system 1 of this embodiment differs from that of the first embodiment in that the controller main unit 28 controls the AOM 13 when the spot area is changed.

Identical symbols are assigned below to portions having the same configurations as those in the light stimulation device 3 and the microscope system 1 of the first embodiment, and a description thereof will be omitted.

When the spot area is changed by means of the mouse 26 or the keyboard 27 while keeping the number of spots of stimulation light constant, the controller main unit 28 causes the AOM 13 to increase or decrease the amount of stimulation light to be made to enter the LCOS-SLM 17 in direct proportion to the increase or decrease in the spot area, such that the amount of stimulation light to be radiated onto each spot before and after the change in the spot area becomes constant.

In this case, the controller main unit 28 increases or decreases the amount of stimulation light to be made to enter the LCOS-SLM 17 in direct proportion to an increase or decreases in the number of pixels of the LCOS-SLM 17 that correspond to the spots.

According to the thus-configured light stimulation device 3 and microscope system 1 of this embodiment, when the spot area is increased while keeping the number of spots of stimulation light constant, the AOM 13 increases the amount of stimulation light in direct proportion to the increase in the number of pixels of the LCOS-SLM 17 that correspond to the spots. On the other hand, when the spot area of stimulation light is decreased, the AOM 13 decreases the amount of stimulation light in direct proportion to the decrease in the number of pixels of the LCOS-SLM 17 that correspond to the spots. Therefore, it is possible to easily increase or decrease the area of a stimulated spot while keeping the irradiation power for each stimulated spot constant.

This embodiment can be modified as described below.

As one modification, the controller main unit 28 may have a table (not shown) in which the spot area of stimulation light is associated with the amount of stimulation light for each spot and may control the AOM 13 according to this table.

This table may be obtained such that, for example, when the spot area is changed to $S_1$, $S_2$, $S_3$, . . . , and $S_{max}$ while keeping the number of spots constant, the amounts of stimulation light $Z_1$, $Z_2$, $Z_3$, . . . , and $Z_{min}$ for each spot per unit area are measured by a light power meter or the like, and the measured values are associated with the spot areas of stimulation light. The amount of stimulation light for each spot per unit area can be measured such that, for example, with an optical mask, such as a pinhole, whose area is known, located at the position of the specimen S, the amount of light transmitted through the optical mask is measured by a light power meter or the like.

For example, when the spot area is changed from $S_1$ to $S_2$ while keeping the number of spots constant, the controller main unit 28 causes the AOM 13 to multiply the amount of stimulation light to be made to enter the LCOS-SLM 17 by $Z_1/Z_2$ based on the table. Specifically, if the amount of stimulation light to be made to enter the LCOS-SLM 17 when the spot area is $S_1$ is $Q_1$, the amount of stimulation light $Q_2$ to be made to enter the LCOS-SLM 17 when the spot area is changed to $S_2$ can be obtained by multiplying $Q_1$ by $(Z_1/Z_2)$.

By doing so, even if an increase or decrease in the spot area of stimulation light and an increase or decrease in the irradiation power to be distributed to each spot do not have an inversely proportional relationship, it is possible to easily and accurately correct the irradiation power for each spot, including an error slightly deviating from the inversely proportional relationship.

In the table, the spot area of stimulation light may be associated with the amount of stimulation light to be made to enter the LCOS-SLM 17.

Although the embodiments of the present invention have been described in detail above with reference to the drawings, specific configurations are not limited to those embodiments, and design changes or the like within a range that does not depart from the scope of the present invention are also encompassed. For example, the present invention is not limited to those applied to the above-described embodiments and modifications, and may be applied to an embodiment in which the above-described embodiments and modifications are appropriately combined: it is not particularly limited.

For example, when the number of spots of stimulation light and the spot area are both changed, the controller main unit 28 may control the AOM 13 such that the amount of stimulation light to be radiated onto each spot before and after the changes in the number of spots and in the spot area becomes constant.

In this case, for example, the controller main unit 28 may cause the AOM 13 to increase or decrease the amount of stimulation light to be made to enter the LCOS-SLM 17 in direct proportion to an increase or decrease in the number of pixels of the LCOS-SLM 17 that correspond to the spots. Furthermore, the controller main unit 28 may have a table (not shown) in which the number of spots of stimulation light and the spot area are associated with the amount of stimulation light for each spot, and may cause the AOM 13 to increase or decrease the amount of stimulation light to be made to enter the LCOS-SLM 17 according to this table. By doing so, it is possible to easily increase or decrease the number of stimulated spots and the area of a stimulated spot while keeping the irradiation power for each stimulated spot constant.

Furthermore, in the above-described embodiments and modifications thereof, a description has been given of a case in which the transmission-type LCOS-SLM 17, which allows stimulation light to be transmitted therethrough and modulates the phase thereof, is used as a phase modulating section; however, instead of this, for example, a reflection-type LCOS-SLM that reflects stimulation light and modulates the phase thereof may be adopted.

Furthermore, in the above-described embodiments, the LCOS-SLM 17 is adopted as a phase modulating section, thereby forming stimulated spots on the specimen S; however, instead of this, for example, an acousto-optic deflector (AOD) may be adopted to form stimulated spots on the specimen S.

REFERENCE SIGNS LIST 1 microscope system
3 light stimulation device
5 imaging device
13 AOM (light-amount adjusting section)
17 LCOS-SLM (phase modulating section)
23 objective lens
26 mouse (spot specifying section)
27 keyboard (spot specifying section)
28 controller main unit (pupil-modulation-pattern determining section, light-amount control section, image forming section)
37 scanner (scanning section)
K table
S specimen

The invention claimed is:

1. A light stimulation device comprising:
   an objective lens that radiates light emitted from a light source onto a specimen;
   a phase modulating section that is located at a position conjugate to a pupil of the objective lens and that is configured to modulate the phase of light to be made to enter the objective lens, based on a predetermined pupil modulation pattern;
   a light-amount adjusting section that adjusts an amount of light to be made to enter the phase modulating section;
   a spot specifying section that is used to specify a number of spots and/or a spot area and a spot position of light to be radiated onto the specimen by the objective lens;
   a pupil-modulation-pattern determining section that determines the predetermined pupil modulation pattern for the phase modulating section according to the number of spots and/or the spot area and the spot position specified by the spot specifying section; and
   a light-amount control section that controls the light-amount adjusting section such that, when the number of spots and/or the spot area specified by the spot specifying section is changed, the irradiation power for each spot before and after the change in the number of spots and/or the spot area becomes constant.

2. A light stimulation device according to claim 1, wherein the light-amount control section controls the light-amount adjusting section so as to increase or decrease the amount of light to be made to enter the phase modulating section in direct proportion to an increase or decrease in the number of spots and/or the spot area.

3. A light stimulation device according to claim 1, wherein the light-amount control section controls the light-amount adjusting section based on a table in which the number of spots and/or the spot area is associated with a value indicating the amount of light to be made to enter the phase modulating section.

4. A microscope system comprising:
   an imaging device that includes:
      a scanning section that scans excitation light emitted from a light source on a specimen; and
      an image forming section that detects return light returning from the specimen when the excitation light is scanned by the scanning section and that forms an image of the specimen; and
   the light stimulation device according to claim 1.

* * * * *